United States Patent

Tung et al.

[11] Patent Number: 5,869,673
[45] Date of Patent: Feb. 9, 1999

[54] PROCESS FOR 3-(2-(7-CHLORO-2-QUINOLINYL)ETHENYL) - BENZALDEHYDE

[75] Inventors: Hsien Hsin Tung, Edison; David Michael Hobbs, Piscataway, both of N.J.

[73] Assignee: Merck & Co., Inc., Rahway, N.J.

[21] Appl. No.: 12,283

[22] Filed: Jan. 23, 1998

Related U.S. Application Data

[60] Provisional application No. 60/039,481 Feb. 28, 1997.

[51] Int. Cl. [6] .................................................. C07D 215/36
[52] U.S. Cl. ............................ 546/172; 546/152; 546/175
[58] Field of Search .................................... 546/172, 152, 546/175

[56] References Cited

U.S. PATENT DOCUMENTS

| | | | |
|---|---|---|---|
| 4,851,409 | 7/1989 | Young et al. | 546/152 |
| 4,883,878 | 11/1989 | Amato et al. | 546/172 |
| 5,281,593 | 1/1994 | Gilmore et al. | 514/249 |
| 5,428,171 | 6/1995 | Young et al. | 546/175 |

*Primary Examiner*—Keith D. MacMillan
*Attorney, Agent, or Firm*—Mollie M. Yang; David L. Rose

[57] ABSTRACT

The yield of monoaldehyde

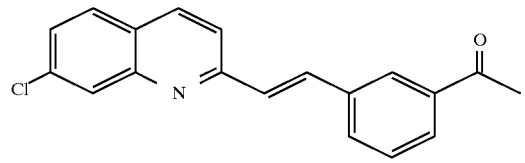

from 7-chloroquinaldine and isophthalaldehyde is increased to about 82% by using a 2 molar excess of isophthalaldehyde, conditions favoring precipitation of product during the reaction and recycling unreacted isophthalaldehyde. The recycling leads to a reduced net consumption of about 1.2 molar equivalents of isophthalaldehyde.

1 Claim, No Drawings

PROCESS FOR 3-(2-(7-CHLORO-2-QUINOLINYL)ETHENYL)-BENZALDEHYDE

CROSS REFERENCE TO RELATED APPLICATIONS

This application is based on, and claims priority from, provisional application 60/039,481 filed on Feb. 28, 1997.

SUMMARY OF THE INVENTION

This invention is concerned with a novel process for the synthesis of 3-(2-(7-chloro-2-quinolinyl)ethenyl)-benzaldehyde (referred to in what follows as monoaldehyde III), an intermediate in the manufacture of montelukast sodium, whereby the effective yield of monoaldehyde is significantly increased. This latter compound is an important leukotriene antagonist useful in the treatment of asthma and related disorders. The chemical step can be depicted as follows:

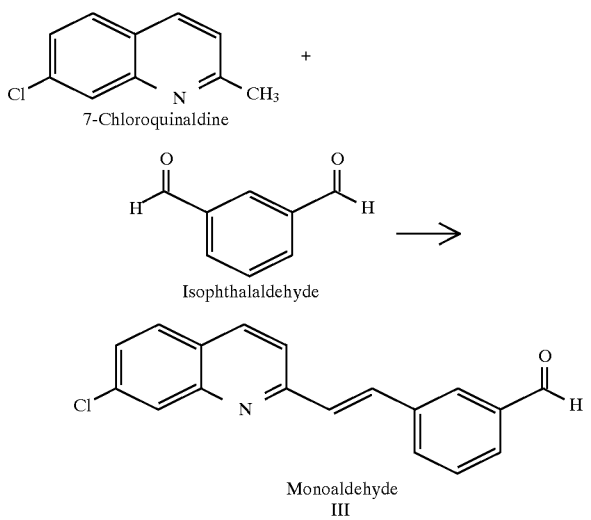

This invention is particularly concerned with providing a reaction environment conducive to crystallization of monoaldehyde during the reaction and crystallization of both monoaldehyde and unreacted isophthalaldehyde at the end of the reaction followed by isolation of these two materials by filtration, followed by dissolution of the isophthalaldehyde in the filter cake and refiltering and recycling the mother liquors to the next batch. By this two-filtration process and recycle of starting material, a significant increase in yield of monoaldehyde and a reduction in usage of the raw material, isophthalaldehyde, are realized.

BACKGROUND OF THE INVENTION

Montelukast sodium (USP Dictionary of USAN and International Drug Names, 1990) has structural formula IV:

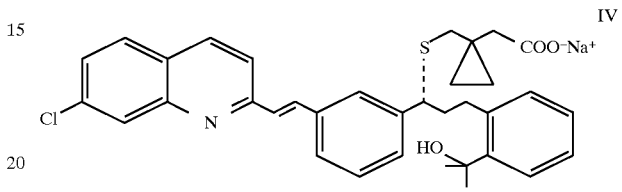

It is a leukotriene antagonist useful in the treatment of asthma and related problems. Its synthesis is fully described in European Patent publication 0 480,717. An important intermediate in the synthesis of montelukast sodium is the monoaldehyde of Structure III shown above. A process for the preparation of this monoaldehyde is described in U.S. Pat. No. 4,851,409 by Young et al. During the development of the overall process for the manufacture of montelukast sodium a much improved process for the monoaldehyde step was developed resulting in a yield of about 65% and a consumption of about 1.5 equivalents of isophthalaldehyde per equivalent of 7-chloroquinaldine.

Now with the present invention there is provided a process whereby the yield of monoaldehyde is increased from 65% to about 82% and the rate of consumption of isophthalaldehyde is reduced from about 1.5 equivalents to about 1.2 equivalents per equivalent of 7-chloroquinaldine.

DETAILED DESCRIPTION OF THE INVENTION

The overall chemical process of this invention and competing process is shown as follows:

(A) MONOALDEHYDE FORMATION REACTION

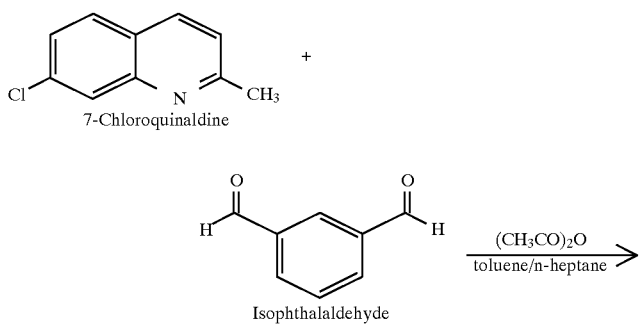

-continued

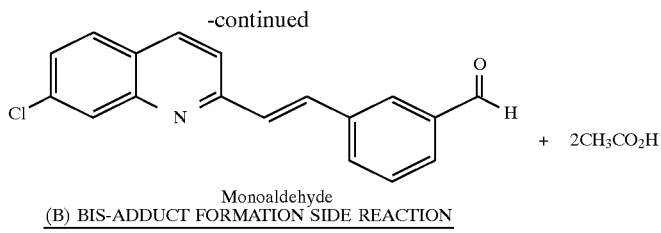

Monoaldehyde (B) BIS-ADDUCT FORMATION SIDE REACTION

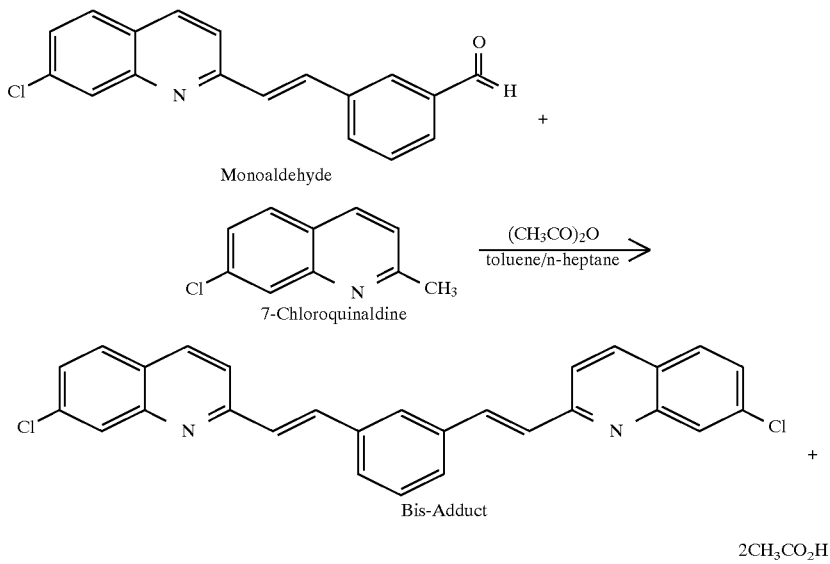

THE REACTION

The use of a mixed solvent of n-heptane and toluene, instead of pure xylene or n-butyl acetate as in previous processes is a key change. It induces crystallization of the monoaldehyde product during the reaction which improves reaction selectivity, i.e., reduces the availability of the monoaldehyde to react with 7-chloroquinaldine in competing reaction (B). A higher reaction yield is positively realized when the solid phase is present during the reaction. The increase is observed at a higher n-heptane percentage, a lower reaction temperature, and a higher reaction concentration, all of which favor precipitation of solids.

If the n-heptane volume percentage is greater than 90 vol %, a second liquid phase appears. At 80 vol % n-heptane, the slurry appears to be slimy. At 50 vol % n-heptane, the reaction solution is homogeneous. The optimum solvent ratio is 75 n-heptane/25 toluene vol %.

The optimum reaction concentration is about 4–8 mL of solvent per gram of 7-chloroquinaldine. Although higher concentrations favor precipitation of the product they also increase color formation.

The reaction time is about 6–13 hours at a reaction temperature of about 99°–120° C. Crystallization begins after about 6–10 hours into the reaction time.

CRYSTALLIZATION

Following completion of the reaction, the mixture is cooled to between 0° C. and −15° C. to promote crystallization. Additional solvent mixture is usually added during the cool-down to permit proper agitation.

FIRST (CRUDE FILTRATION)

The cold slurry is filtered and the filter cake is washed with about one bed volume of solvent mixture. The mother liquors and wash solvents containing acetic anhydride, acetic acid, and other impurities are discarded.

SECOND (PURE FILTRATION)

The filter cake, wet with the solvent mixture is slurried in toluene at room temperature and filtered. The filter cake is washed with a small amount of toluene.

The monoaldehyde filter cake is used directly in the next step in the synthesis of montelukast sodium.

The filtrate from the second filtration is concentrated and the residue consisting of unreacted isophthaldehyde and a small amount of monoaldehyde is recycled to the next batch.

EXAMPLE 1

Detailed Description of Process of the Invention

The following process description is representative of each batch, or cycle, of 6-cycles of a process wherein unreacted starting material from one cycle is recycled to the next cycle.

REACTION:

A mixture of isophthalaldehyde, 7-chloroquinaldine and monoaldehyde (recycled from previous batch) in molar ratios of 3/1/0.12–0.13 was dissolved in a solvent mixture comprising 75 vol % n-heptane and 25 vol % toluene. The amount of solvent employed was 6.4 mL/g of 7-chloroquinaldine. Acetic anhydride (1.5 mol/mol of 7-chloroquinaldine was added and the mixture was agitated in an inert atmosphere while heating to and maintaining the temperature of 99°–101° C. over a period of 13 hours. Crystallization occurred after about 8–10 hours into the reaction time.

CRYSTALLIZATION:

The heat source was removed and additional solvent mixture (12.8 mL/g of 7-chloroquinaldine) was added over a period of about 2 hours during which time the temperature dropped to about 80° C. The batch was then cooled with agitation to about 0°–2° C. over about 6–8 hours and held at 0°–2° C. for about 0–2 hours.

FIRST FILTRATION:

The cold batch was filtered and the filter cake was washed with the n-heptane/toluene solvent mixture (10 mL/g 7-chloroquinaldine).

SECOND FILTRATION:

The wet (solvent) filter cake from the first filtration was slurried in toluene (22 mL/g 7-chloroquinaldine) for 1–2 hours at 19°–21° C. and filtered. The filter-cake was washed with toluene (10 mL/g of 7-chloroquinaldine).

The combined filtrate and wash was decolorized with Darco (0.1–0.2 g/g of 7-chloroquinaldine). After separation of the Darco the filtrates and wash were concentrated and the residue was recycled to the next batch.

The results of six cycles of the above procedure are shown in Table I.

EXAMPLE 2

Detailed Description of a Previous Process

To a 50-liter, 3-neck flask equipped with a mechanical stirrer, thermometer and addition funnel was added xylene (16 liters), 7-chloroquinaldine (3000 grams, 16.89 moles), isophthalaldehyde (3398 grams, 25.34 moles), and acetic anhydride (4.69 liters, 49.7 moles).

The reaction mixture was heated at reflux until assay indicated the reaction was complete (about 7 hrs).

The reaction mixture was allowed to cool to about 40° C. overnight. The reaction mixture became very thick as the desired product and the by-product (bis-adduct) crystallized from the reaction mixture. Good mechanical stirring was required. Hexanes (16 liters) were then added and after cooling to 21°–23° C. the reaction mixture was filtered. The collected solid was washed with hexanes (16 liters) and dried in vacuo to give the crude product (4470 grams, about 4:1 mixture of desired product:bis-adduct).

In a 72 liter 3-neck flask equipped with mechanical stirring and a thermometer was placed ethyl acetate (40 liters) and one-half of the crude product (2235 grams). The mixture was heated to reflux for 30 minutes and the very insoluble bis-adduct was removed by filtration through a preheated, jacketed sintered glass funnel into a 50 liter 3-neck flask equipped with mechanical stirring and a vacuum take off. The filtrate was then concentrated in vacuo at ≦40° C. to a volume of about 15 liters. The resulting slurry was heated to reflux and then gradually cooled to 0° C.–4° C. over a 6–12 hr period. After aging at 0° C.–4° C. for 2 hrs the product was filtered and the filter cake was washed with cold ethyl acetate (5 liters, 0° C.–5° C.) and dried overnight in vacuo (45° C.). Repetition of the recrystallization on the remaining crude product (2235 grams) as above afforded crystalline monoaldehyde (combined total= 3228 grams, ≧98 weight % pure by HPLC. 65% yield based on 7-chloroquinaldine).

EXAMPLE 3

Detailed Description of a Previous Process

A mixture of 1 g of 7-chloroquinaldine, dry n-butyl acetate (5.333 mLs/g 7-chloro), isophthalaldehyde (1.133 g/g 7-chloro, 1.5 equivalents) and acetic anhydride (0.0862 g/g 7-chloro, 1.5 equivalents) was heated to and maintained at reflux (138° C.) for 8 hours. Some bis-adduct crystallized at about 4 hours. The batch was cooled to and held at 90° C. for 1 hour, cooled to 80° C. and seeded with solid monoaldehyde, and held at 80° C. for 1.5 hours. The batch was cooled to 70° C. over 2 hours, 50° C. over 2 hours and 15° C. over 2 hours where it was held for 2 hours. The precipitated monoaldehyde/bis-adduct was collected by filtration and the filter cake was washed with 15° C. n-butyl acetate (2.667 mLs/g 7-chloro). The yield was about 65%.

TABLE I

| Cycle | Yield (%) | Product | | 1st Filtrate Loss | | 2nd Filtrate Recovery | | Initial Mole Ratio iso/7-chloro/Mono |
| | | mono wt (%) | iso wt (%) | mono mol (%) | iso mol (%) | mono mol (%) | iso mol (%) | |
| --- | --- | --- | --- | --- | --- | --- | --- | --- |
| 1 | 80.56 | 88.77 | 0.10 | 2.24 | 21.84 | 9.23 | 163.00 | 3/1/0.15 |
| 2 | 83.50 | 89.96 | 0.27 | 1.53 | 20.83 | 13.52 | 188.05 | 3/1/0.09 |
| 3 | 81.56 | 90.21 | <0.1 | 2.31 | 24.34 | 12.83 | 149.83 | 3/1/0.135 |
| 4 | 82.90 | 88.74 | 2.90 | 2.03 | 19.04 | 13.96 | 204.76 | 3/1/0.128 |
| 5 | 82.39 | 89.66 | 0.21 | 2.30 | 20.70 | 13.83 | 185.61 | 3/1/0.125 |
| 6 | 82.11 | 90.98 | 0.17 | 2.34 | 20.25 | 14.89 | 174.65 | 3/1/0.128 |
| Ave | 82.17 | 89.72 | 0.61 | 2.12 | 21.17 | 13.04 | 177.65 | 3/1/0.126 |

Note:
1. All mole percentage calculations are based upon 7-chloro charge, except wt % of the product.
2. 1st filtrate loss includes the vessel rinse (physical handling loss).

What is claimed is:

1. In a process for the preparation of monoaldehyde III of formula:

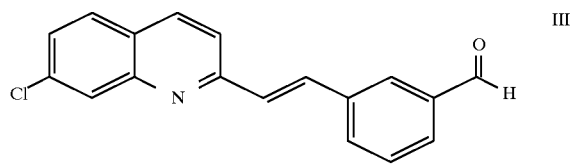

comprising reacting 1 molar equivalent of 7-chloroquinaldine (I) with 1.5 molar equivalents of isophthalaldehyde (II)

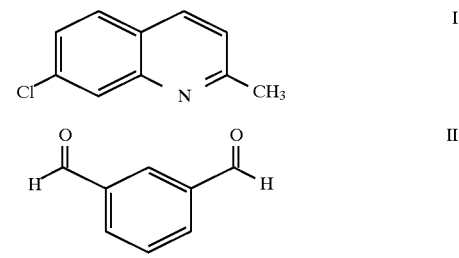

in the presence of acetic anhydride and optionally a solvent at reflux temperature until the reaction is substantially complete, and collecting the product and bis-adduct of structure

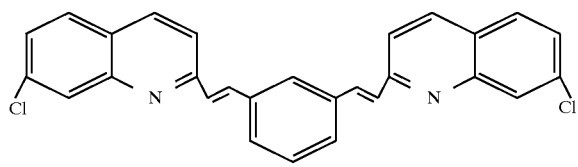

on a filter wherein the improvements comprise:

(a) using 3 molar equivalents of isophthalaldehyde;
(b) using a solvent mixture of n-heptane/toluene (3/1/v/v);
(c) washing the filter cake of monoaldehyde and unreacted isophthalaldehyde with toluene; and
(d) recycling the washes containing unreacted isophthalaldehyde to the next batch;

whereby the yield of product is increased from about 65% to about 82%; and the usage of isophthalaldehyde is reduced from 1.5 molar equivalents to 1.2 molar equivalents.

* * * * *